(12) United States Patent
Kim et al.

(10) Patent No.: US 8,658,421 B2
(45) Date of Patent: Feb. 25, 2014

(54) CIRCULATORY PHOTOBIOREACTOR

(75) Inventors: Kwang Ho Kim, Dangjin-gun (KR);
Hee-Gyoo Kang, Seoul (KR); Young Il Kwon, Daejeon-si (KR); Sun Jong Kim, Anyang-si (KR); Hee Joung Lim, Seoul (KR); Mi Jeong Kim, Seongnam-si (KR)

(73) Assignees: Kairos Global Co., Ltd., Seoul (KR);
Eulgi University Industry Academy Cooperation Foundation, Seoul (KR)

( * ) Notice: Subject to any disclaimer, the term of this patent is extended or adjusted under 35 U.S.C. 154(b) by 613 days.

(21) Appl. No.: 12/842,576

(22) Filed: Jul. 23, 2010

(65) Prior Publication Data

US 2012/0021505 A1 Jan. 26, 2012

(51) Int. Cl.
*C12N 1/12* (2006.01)
*C12M 1/00* (2006.01)
*C12M 3/00* (2006.01)
*A01G 7/00* (2006.01)
*A01G 9/00* (2006.01)
*A01H 13/00* (2006.01)

(52) U.S. Cl.
USPC .............. 435/292.1; 435/257.1; 435/289.1; 47/1.4; 47/17

(58) Field of Classification Search
USPC ......... 435/292.1, 257.1, 283.1–309.4; 47/1.4, 47/17
See application file for complete search history.

(56) References Cited

U.S. PATENT DOCUMENTS

2007/0231886 A1 10/2007 Kahlert et al.
2008/0220514 A1 9/2008 Lu
2008/0311649 A1 12/2008 Cloud et al.
2010/0028977 A1* 2/2010 Ng et al. .............. 435/257.1
2010/0068779 A1* 3/2010 Wells et al. .............. 435/167
2010/0279389 A1* 11/2010 Ziller .................. 435/257.1

FOREIGN PATENT DOCUMENTS

| CN | 2234443 Y | 9/1996 |
| CN | 101597567 A | 12/2009 |
| JP | 05-023166 | 2/1993 |
| JP | 09-121835 | 5/1997 |
| JP | 52-108082 | 9/1997 |
| JP | 2009-195163 | 3/2009 |
| JP | 3151710 | 6/2009 |
| KR | 10-0235182 B1 | 9/1999 |
| KR | 10-2002-0057882 A | 7/2002 |
| KR | 10-2002-0083558 A | 11/2002 |
| KR | 10-2004-0019298 A | 3/2004 |
| KR | 10-0679989 B1 | 2/2007 |
| KR | 10-0818203 | 3/2008 |
| KR | 10-2010-0113179 | 10/2010 |
| WO | 02/086053 A1 | 10/2002 |
| WO | WO 2009142765 A2 * | 11/2009 |

* cited by examiner

*Primary Examiner* — Nathan Bowers
*Assistant Examiner* — Lydia Edwards
(74) *Attorney, Agent, or Firm* — Stuart H. Mayer; Mayer & Williams PC

(57) ABSTRACT

A circulatory photobioreactor is provided. The circulatory photobioreactor comprises a first cultivating part, a second cultivating part and a pump part connecting the first cultivating part and the second cultivating part. The first cultivating part comprises a culture tank in which culture media are supplied and a first light source coupled to the culture tank, which illuminates the inside of the culture tank. The second cultivating part comprises a culture pipe placed outside of the culture tank and supplied with cultures from the culture tank and a second light source coupled to the culture pipe, which illuminates the inside of the culture pipe. The pump part is connected to both the first cultivating part and the second cultivating part in order to circulate the culture solution between them.

17 Claims, 4 Drawing Sheets

CIRCULATORY PHOTOBIOREACTOR

BACKGROUND OF THE INVENTION

1. Field of the Invention

The following description relates to a culture apparatus, particularly to a circulatory photobioreactor.

2. Description of the Related Art

Currently, crops cultivated world-wide are used as major food sources for humans. However, yield per acre is not too high and the energy efficiency of solar power is extremely low. On the contrary, photosynthetic microalgae capable of growing underwater with solar energy, carbon dioxide and the use of inorganic salts are favorable since they can be cultivated in areas in which crops do not grow. This provides at least 20 times proteins per acre more than conventional crops and can provide various useful substances and rare natural substances which are not produced in microorganisms, animals and plants. In particular, since algae whose cell size is large precipitate well, isolating them and extracting some substances therefrom is easy. In addition, they use solar energy as a major energy source; thus it is possible to use solar energy efficiently. Further, since they use carbon dioxide as carbon sources and have a photosynthetic system producing oxygen as byproducts, they can alleviate air pollution.

Accordingly, photosynthetic microalgae including genus *Chlorella*, genus *Dunaliella* and genus *Spirulina*, particularly microalgae belonging genus *Spirulina* (hereinafter referred to as "*Spirulina*"), is studied vigorously since it is bigger than other photosynthetic microalgae, grows easily in alkali-contaminated environment and can be applied in food, pharmaceutical and other industries. In the meanwhile, temperate regions such as Korea having climate characteristics such as the occurrence of four seasons, dramatic variations of seasonal temperature and sunshine are developing indoor culture technology rather than outdoor culture technology.

For example, Korean Patent No. 235182 discloses a continuing culture apparatus comprising automatic control heater, a culture vessel having an aeration apparatus, a frame having equipments for supporting the culture vessel, a medium-supplying pipe coupled to the side of the frame, a rubber tube for circulating culture solution and a water pump for circulating the culture solution. Korean Patent Gazette No. 2004-0019298 discloses an apparatus for cultivating microalgae comprising a culture vessel molded as a double cylinder-type device consisting of an inner cylinder deposited horizontally and an outer cylinder, wherein at least the outer cylinder comprises a transparent material transmitting light and a gas inlet is opened at the bottom of the culture vessel. Korean Patent No. 679989 discloses a watercourse-type outdoor culture vessel for microalgae in which an inoculation culture vessel for cultivating inoculates is installed and integrated. However, if one cultivates *Spirulina* using those apparatuses, the grown *Spirulina* attaches to the surface of the culture vessel excessively. Accordingly, the culture efficiency decreases and one cannot obtain favorable cultural products due to contamination by various germs.

In order to solve the above problems, a method comprising sealing a culture vessel and preventing contamination by various germs by filtering air supplied using a filter was developed. For example, Korean Patent Gazette No. 2002-0057882 discloses an outdoor large scale culture apparatus comprising a device for filtering and UV sterilizing, an air pump, a filtering device, a guide pipe, a filter, a needle valve and a culture vessel and Korean Gazette Patent No. 2002-0083558 discloses a high-density culturing apparatus comprising a culture vessel having a cover on the top side and a pH sensor and dispenser in the culture vessel, a frame for the culture vessel having fluorescent lights, a pH controller, an air pump and a $CO_2$ culture tank.

SUMMARY OF THE INVENTION

It is possible to prevent contamination by various germs using various apparatuses of the prior art, however, the problems that excessive photosynthetic microalgae attach to the inner surface of the culture vessels and the cultivation efficiency decreases are not solved until now. If the problems are solved, it is possible to improve the cultivation efficiency of photosynthetic microalgae remarkably. However, there is no report teaching such a solution. Thus, the purpose of the present invention is to provide a novel culture apparatus for cultivating microalgae and capable of preventing attachment of photosynthetic microalgae to an inner surface of a culture vessel and improving the cultivation efficiency thereby.

The present inventors have determined that when the area in which the culture solution is exposed to light is maximized grown photosynthetic microalgae do not attach to the inner surface of the culture vessel when the photosynthetic microalgae are cultivated in a circular way.

In an aspect, the present invention provides a circulatory photosynthetic bioreactor comprising the following:
 a first cultivating part comprising a culture tank in which culture media are supplied and a first light source is coupled to the culture tank so as to illuminate the inside of the culture tank;
 a second cultivating part comprising a culture pipe is placed outside the culture tank and supplied with culture solution from the culture tank and a second light source is coupled to the culture pipe so as to illuminate the inside of the culture pipe; and
 a pump part is connected to both the first cultivating part and the second cultivating part so as to circulate the culture solution between the first cultivating part and the second cultivating part.

In an embodiment, the first light source is placed inside the culture tank, but is not limited thereto. In an embodiment, the second light source is coupled to the inner surface of the culture pipe or placed outside the culture pipe in the longitudinal direction of the culture pipe, but is not limited thereto. In another embodiment, the culture pipe preferably has a parallel multiple folded form and comprises a plurality of second light sources coupled to the outside of the culture pipe in the longitudinal direction of the culture pipe, but is not limited thereto. In a preferred embodiment the culture pipe has an inside diameter of 3 to 30 cm. In a more preferred embodiment the diameter is 5 to 20 cm. In the most preferred embodiment the diameter is 10 to 15 cm. In a preferred embodiment, the first cultivating part further comprises at least one first culture solution inlet and at least one first culture solution outlet connected to both the culture tank and the pump part, and the second cultivating part further comprises at least one second culture solution inlet and at least one second culture solution outlet connected to the first culture solution outlet and to the second culture solution inlet, respectively through the pump part, but is not limited thereto. In another preferred embodiment, the first cultivating part further comprises a fresh media inlet for supplying fresh media into the culture tank and a final outlet for releasing culture solution from the culture tank, but is not limited thereto, and the fresh media inlet preferably has a spray ball shape including a globular type end and a plurality of micro nozzles on the globular type end, but is not limited thereto.

In an embodiment, the first cultivating part further comprises an agitator for mixing culture solution, which is attached to the inside of the culture tank, but is not limited thereto. In another embodiment, the first cultivating part further comprises a pressure controlling valve for controlling pressure in the culture tank and the pressure controlling valve is preferably a one-way valve which opens by pressure of oxygen generated during the cultivation of photosynthetic microalgae.

In an embodiment, the first cultivating part further comprises a temperature controller for controlling temperature in the culture tank and the temperature controller is preferably a water-jacket coupled to the outside of the culture tank, but is not limited thereto.

In an embodiment, the first cultivating part further comprises one or more ports for sensors coupled to the culture tank, but is not limited thereto. In another embodiment, the first cultivating part further comprises a gas inlet coupled to the culture tank so as to inject gases into the culture tank, but is not limited thereto.

In an embodiment, the second cultivating part further comprises an oxygen discharger and the oxygen discharger preferably comprises an earth sensor, a mass flow controller electrically connected to the earth sensor and a valve connected to the mass flow controller, but is not limited thereto.

In a preferred embodiment, a flow rate controller is coupled to the pump part in order to control the flow rate of a culture solution circulating the second cultivating part. In a more preferred embodiment, the flow rate controller is built in the pump part.

In another aspect, the present invention provides a circulatory photosynthetic bioreactor comprising:
  a first cultivating part comprising a culture tank in which culture media are supplied, a first media inlet, a first media outlet and a first light source coupled each to the culture tank;
  a second cultivating part comprising a culture pipe arranged outside the culture tank in a tubular shape and supplied with culture media from the culture tank, a second media inlet, a second media outlet and a second light source each coupled to the culture pipe, wherein the first media outlet is connected to the second media inlet and the first media inlet is connected to the second media outlet in order that the culture media can circulate between the first cultivating part and the second cultivating part.

The photosynthetic bioreactor may further comprise a pump part connecting the first cultivating part and the second cultivating part so as to circulate a culture solution between the first cultivating part and the second cultivating part.

In a preferred embodiment, the pump part further comprises a flow rate controller electronically coupled to a pump thereof. In a more preferred embodiment the flow rate controller is built in the pump part. In a preferred embodiment the culture pipe has an inside diameter of 3 to 30 cm. In a more preferred embodiment the diameter is 5 to 20 cm. In the most preferred embodiment the diameter is 10 to 15 cm.

The circulatory photobioreactor of the present invention prevents attachment of photosynthetic microalgae on the inner surface of a culture vessel and can increase the culture efficiency of the photosynthetic microalgae thereby. Accordingly, one can cultivate photosynthetic microalgae economically.

In the description, "culture media" or "culture medium" means media for the cultivation without any living organism such as microalgae, whereas "culture solution" means a mixture of the culture media and microalgae to be cultivated.

BRIEF DESCRIPTION OF THE DRAWINGS

The accompanying drawings, together with the specification, illustrate exemplary embodiments of the present invention and, together with the description, serve to explain the principles of the present invention.

DETAILED DESCRIPTION OF THE INVENTION

Figure 1:
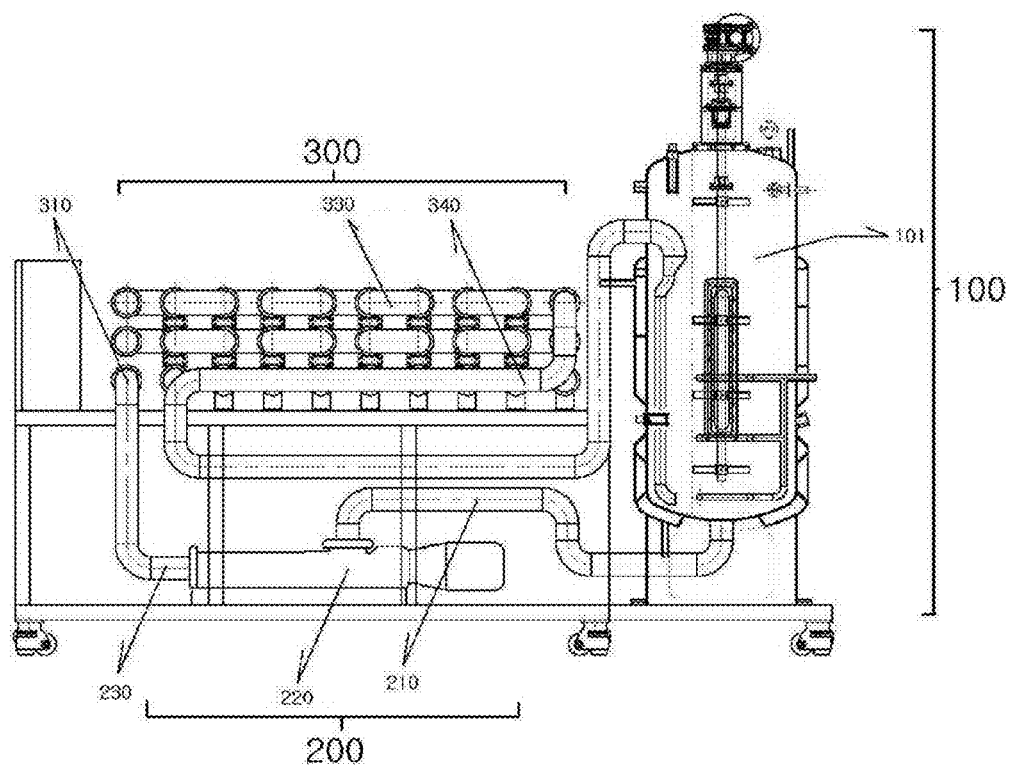
FIG. 1 is a schematic diagram showing a photobioreactor according to an embodiment of the present invention.

In the following detailed description, only certain exemplary embodiments of the present invention are shown and described, by way of illustration. As those skilled in the art would recognize, the invention may be embodied in many different forms and should not be construed as being limited to the embodiments set forth herein. Also, in the context of the present application, when an element is referred to as being "on" another element, it can be directly on another element or be indirectly on another element with one or more intervening elements interposed therebetween. Like reference numerals designate like elements throughout the specification.

The present inventors performed various experiments in order to investigate the reason why cultivated photosynthetic microalgae attach on the inner surface of culture vessels. As a result the two reasons are confirmed; one is recognized as the proliferation of microalgae along with the growth thereof according to applying periodic conditions of light and dark and the other is the recognition that photosynthetic microalgae are coupled on the site where flow velocity is low because the flow of culture solution is restricted locally and then the site of attachment is expanded.

The present inventors tried to design a culture vessel capable of lowering proliferating rate of photosynthetic microalgae and securing proper flow of culture solution by applying only light condition however, it is impossible to obtain a proper flow of culture solution even though raising the stirring rate with a culture tank-type photobioreactor having an agitator.

Thus, the present inventors tried to run the culture solution containing photosynthetic microalgae using other methods rather than using only an agitator and confirmed that circulating the culture solution from the culture tank to a pipe whose two ends are coupled to the culture tank can make the culture solution flow well compared to using only an agitator. Accordingly, the present inventors have invented a photobioreactor having a culture pipe with a light source and a pump in order to solve the above problems. The present inventors could run culture solution at a constant rate using the culture pipe and the pump of said photobioreactor and apply light condition to the culture solution easily along with providing sufficient light to cultivate photosynthetic microalgae through the light source coupled to the culture pipe.

The photobioreactor according to embodiments of the present invention is described in detail as referring to the following drawings described hereinafter:

FIG. 1 is a schematic diagram showing a photobioreactor according to an embodiment of the present invention. As shown in FIG. 1, the photobioreactor may comprise a first cultivating part 100, a pump part 200 and a second cultivating part 300. Photosynthetic microalgae are cultivated via circulation from the first cultivating part 100 to the pump part 200, from the pump part 200 to the second cultivating part and then from the second cultivating part to the first cultivating part 100, since the first cultivating part 100, the pump part 200 and the second cultivating part 300 are connected to each other.

The second cultivating part 300 may be positioned apart from the first cultivating part 100. The first cultivating part 100 may be provided as a cylinder-type as shown in FIG. 1, but is not limited thereto. For example, the shape of the first cultivating part 100 can be deformed into various forms such as a polygonal column. The second cultivating part 300 may be provided as a tubular shape and can include pipes molded with various shapes, etc. The pump part 200 is composed so that the culture solution can circulate between the first cultivating part 100 and the second cultivating part 300. For example, the pump part 200 can be positioned between the first cultivating part 100 and the second cultivating part 300 and can be equipped with a third media inlet 210 connected to a first culture solution outlet 132 of the first cultivating part 100 and can be equipped with a third culture solution outlet 230 connected to a pump 220 and a second culture solution inlet 310 of the second cultivating part 300. Accordingly, the culture solution flowing from the first cultivating part 100 is transferred to the second cultivating part 300 and the culture solution circulates as follows: the first cultivating part 100→the pump part 200→the second cultivating part 300→the first cultivating part 100. The pump part 200 can control the flow rate of culture solution circulating the second cultivating part 300 via a flow rate controller coupled electronically thereto. In a preferred embodiment, the flow rate controller is built in the pump part 200. Control of the flow rate of culture solution is important for successful cultivation of *Spirulina*, because *Spirulina* is a multicellular spiral alga. If the flow rate is low, attachment of *Spirulina* occurs and gas exchange and illumination becomes worse due to inappropriate hydrodynamics. In contrast, a high flow rate results in the loss of useful materials in *Spirulina*. Thus, the flow rate should be controlled properly. It is preferred to control the flow rate between 1 to 50 cm/sec. More preferably the flow rate is 10 to 40 cm/sec. In the most preferred embodiment the flow rate is 20 to 30 cm/sec.

In a preferred embodiment the culture pipe 330 has an inside diameter of 3 to 30 cm. In a more preferred embodiment the inside diameter is 5 to 20 cm. In the most preferred embodiment the inside diameter is 10 to 15 cm. The inside diameter of the culture pipe is important for cultivating Spirulina. If the inside diameter is more than 30 cm, the productivity gets worsen due to inappropriate illumination. In contrast, if the inside diameter is less than 5 cm, it is difficult to scale-up culture volume.

Figure 2:
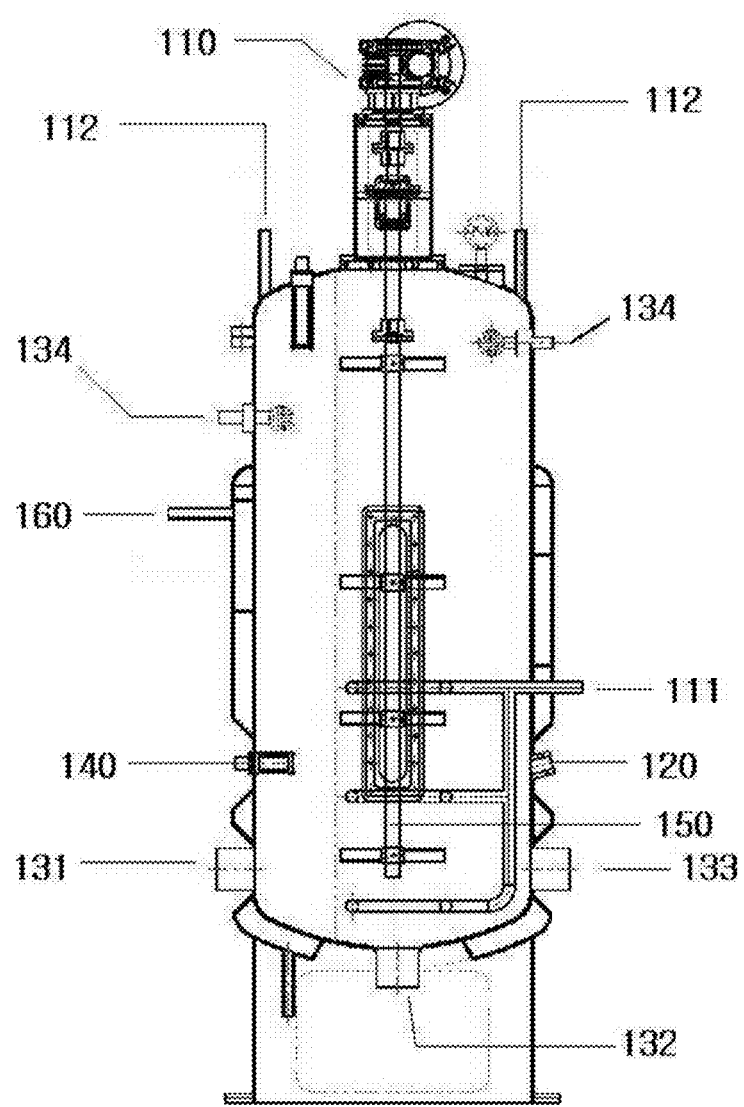
FIG. 2 is a sectional view of the first cultivating part included in the photobioreactor of the present invention.

FIG. 2 is a sectional view of the first cultivating part 100 included in the photobioreactor of the present invention. As shown in FIG. 2, the first cultivating part 100 can be equipped with a cylindrical culture tank 101, an inoculums inlet 110, a gas inlet 111, a port for sensors 120, a first culture solution inlet 131, a first culture solution outlet 132, a final outlet 133, a pressure-controlling valve 112, a fresh media inlet 134, a first light source 140, an agitator 150 and a temperature-controller 160.

For example, the inoculums inlet 110 may be coupled to the upside of the culture tank 101, the gas inlet 111 and the port for sensors 120 may be coupled to the lower part of the culture tank 101. However, the arrangement is provided as one embodiment and may be varied according to changes of the shape of the culture tank 101.

The inoculums inlet 110 may be provided so as to inject various gases such as a mixture of nitrogen and carbon dioxide mixture to the inside of the culture tank 101. Accordingly, it is possible to prevent contamination by various germs originating from the external environment during cultivating of photosynthetic microalgae by maintaining internal positive pressure in the culture tank 101. The positive pressure may be 0.1 to 1.0 kgf/cm$^2$ used for the conventional cultivation of microalgae, but not limited thereto.

The port for sensors 120 can be equipped with various sensors such as a pH sensor, a $CO_2$ sensor, a DO sensor and a temperature sensor.

In the meantime, the culture solution flows into the first cultivating part 100 from the second cultivating part through the first culture solution inlet 131 and flows out of the first cultivating part 100 to the pump part 200 via the first culture solution outlet 132. When the cultivation is finished, the final culture solution is released to the outside of the first cultivating part 100 through the final outlet 133.

In addition, the pressure-controlling valve 112 which is a one-way valve gating by the pressure of oxygen generated by cultivating the photosynthetic microalgae may be composed to be gated to discharge gases externally when the internal pressure is maintained as positive, but to be closed to stop discharging gases when the internal pressure is lowered.

The fresh media inlet 134 is a stick-type tube whose end is a globular shape, and may be provided as a spray ball shape having a plentiful number of micro nozzles on the surface of the globular end. Fresh media can be dispensed in a microspray into the first cultivating part 100 through the spray ball; thus the fresh media inlet 134 functions to eliminate foam generated in the first cultivating part 100. Further, the fresh media inlet 134 may be used for supplying detergents for washing the inside of the first cultivating part 100, the pump part 200 and the second cultivating part 300.

The first light source 140 which is a device for emitting light capable of performing photosynthesis during cultivating photosynthetic microalgae emits three wavelengths of light or five wavelengths of light. In this regard, it is preferred that the intensity of illumination and the light-dark cycle are controlled automatically according to cultivation conditions. For example, the first light source 140 may be placed at the inside of the culture tank 101. In another embodiment, if the culture tank 100 comprises transparent materials or parts of the culture tank 100 are equipped with a transparent window through which light passes, the light source 140 may be placed at the outside of the culture tank 101.

The agitator 150 may be coupled to the inner-lower part and functions in mixing culture solution in a primary culture, and mixing culture mixture remaining in the first cultivating part 100 with culture solution flowing from the first culture solution inlet 131. The temperature controller 160 may be coupled to the outside of the first cultivating part 100 and functions in controlling temperature. The temperature controller may be a water jacket capable of controlling culture temperature by circulating water with appropriate temperature through the jacket, but is not limited thereto. Further, an observation window through which one can check the inside of the first cultivating part 100 may be added.

Figure 3:
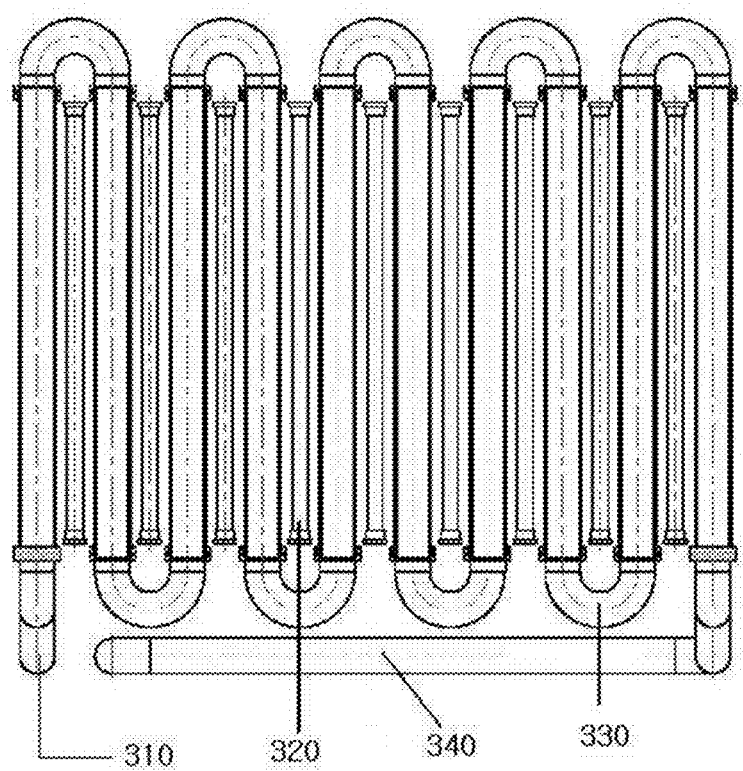
FIG. 3 is a plan view illustrating an embodiment of the second cultivating part included in the tubular photobioreactor.

FIG. 3 is a plan view illustrating an embodiment of the second cultivating part 300 included in the tubular photobioreactor. As shown in FIG. 3, the second cultivating part 300 is equipped with a second culture solution inlet 310 connected to a third culture solution outlet 230 of the pump part 200, a culture pipe 330 and a second culture solution outlet 340 connected to the first culture solution inlet 131 of the first cultivating part 100.

The second light source 320 may be coupled to parts or the whole of the second cultivating part 300. For example, the second light source 320 may be coupled to the outside of the culture pipe 330 and extended longitudinally therethrough. The culture pipe 330 of the second cultivating part 300 functions in circulating culture solution including photosynthetic microalgae and providing an environment where the circulating photosynthetic microalgae perform photosynthesis receiving light from the second light source 320. Thus, the culture pipe 330 may be composed of transparent materials in order to transmit the light emitted from the second light source 330. The whole culture pipe 330 may be composed of only transparent materials or only parts thereof where light passes through are composed of transparent materials. Alternatively, the second light source 320 may be placed in the inside of the culture pipe 330. In this case, the second light source 310 is preferably coupled to the inner surface and is preferably an LED (light-emitting diode) and the culture pipe 330 may be composed of opaque materials. Additionally, sensors such as a pH sensor, a $CO_2$ sensor, a DO sensor, and a temperature sensor may be coupled to one or more sides of the culture pipe 330. Further, the culture pipe 330 is preferably deformed as a narrow and long tubular shape in order to maximize the area exposed to light. In this case, the culture pipe 330 is preferably deformed as a folded structure and the second light source 320 may be provided multiply between the folded structures of the culture pipe 330.

In an embodiment of the present invention, the culture pipe 330 of the second cultivating part 300 may be composed as a parallel multiple folded form including straight parts and curved parts on one frame or such a folded form may be piled up as a multi-layer structure. Also, the frame which is a scaffold for anchoring the second light source 320 may additionally comprises a power supply for the second light source 320. In addition, the second light source 320 functions in emitting light for the photosynthesis of the photosynthetic microalgae during the cultivation. Wavelength emitted from the second light source 320 is preferably three-wavelength or five-wavelength similar to daylight but not limited thereto and it is preferred that the intensity of illumination and the light-dark cycle are controlled automatically according to cultivation conditions.

In the meantime, since the culture pipe 330 is deformed as a multiple folded structure including straight parts and curved parts, oxygen generated during the cultivation of photosynthetic microalgae may be accumulated in the curved parts without being discharged. In order to discharge the accumulated oxygen by force, it is preferable that the culture pipe is additionally equipped with an oxygen discharger at the curved parts. When oxygen is accumulated above a certain level, the accumulated oxygen is discharged via automatic operation of the oxygen discharger (See FIG. 4).

Figure 4:
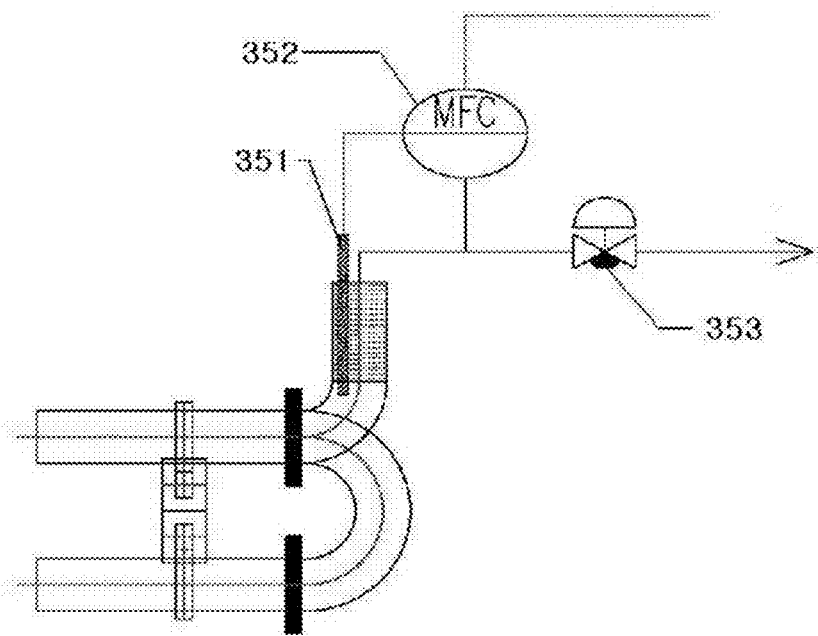
FIG. 4 is a schematic diagram illustrating an embodiment of an oxygen discharger coupled to the culture pipe.

FIG. 4 is a schematic diagram illustrating an embodiment of an oxygen discharger coupled to the culture pipe 330. As shown in FIG. 4, the oxygen discharger comprises an earth sensor 351, a mass flow controller 352 electrically connected to the earth sensor and a valve 353 connected to the mass flow controller 352 and one end of the earth sensor 351 is immersed in the culture solution for applying an electric current.

If a gas layer is formed by the accumulation of oxygen in the curved parts, the earth sensor 351 is exposed from the culture solution and the electricity is interrupted. During the interruption, the valve 353 connected to the mass flow controller 352 is operated and then a certain amount of oxygen is expelled. When the earth sensor is re-immersed in the culture solution according to the discharge of oxygen and the electric current is applied, the valve 353 stops.

In another aspect, the tubular photobioreactor of the present invention may include one cultivating part and two or more pump parts and culture pipe parts.

Figure 5:
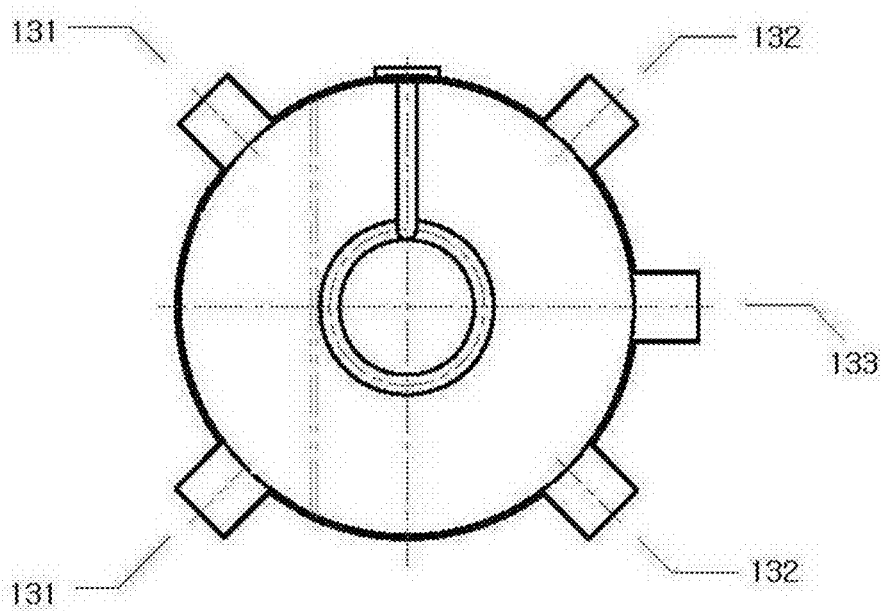
FIG. 5 is a plan view illustrating an embodiment of a cultivating part having two first culture solution outlets.

FIG. 5 is a plan view illustrating an embodiment of a cultivating part having two first culture solution outlet 132 providing culture solution with two pump parts, two first culture solution inlet 131 flowing in the culture solution from two culture pipes 330 and a cultivating part 100. As shown in FIG. 5, using the tubular photobioreactor comprising one cultivating part, two or more pump parts and culture pipe parts, the cultivating part provides the culture solution for the two culture pipe parts and the cultivation would be more efficient thereby.

Hereinafter, the action and the effect of the tubular photobioreactor are described in detail referring to the described drawings:

First of all, the first culture solution inlet 131, the first culture solution outlet 132 and the final outlet 133 of the first cultivating part 100 are closed and an inoculum of microalgal seeds is injected to the culture tank 101 via the inoculums inlet 110 or fresh media inlet 134; then, light is applied from the first light source 140 and a primary culture is performed maintaining appropriate temperature using the temperature controller 160 and operating the agitator 150. The primary culture is terminated at an appropriate time after checking the culture condition using various sensors coupled to the port for sensors 120 of the first cultivating part 100.

Next a fresh media is injected into the culture tank 101 via the fresh media inlet 134 and the agitator 150 is operated continuously for mixing culture solution after the primary culture with the injected fresh media. When equal volumes of fresh media to the primary culture solution are injected into the culture tank 101, the first culture solution inlet 131 and the first culture solution outlet 132 are opened and the mixed culture solution is transferred to the third culture solution inlet 210 of the pump part 200. If the mixed culture solution is transferred to the third culture solution inlet 210 of the pump part 200, the pump 220 of the pump part 200 is operated and the mixed culture solution is transferred to the second culture solution inlet 310 of the second cultivating part 300 via the third culture solution outlet 230. The mixed culture solution transferred to the second culture solution inlet 310 of the second cultivating part 300 is transferred the culture pipe 330, the second culture solution outlet 340 and the first culture solution inlet 131 of the first cultivating part 100, serially via the pump 220 and a circulation (the first cultivating part→the pump part→the second cultivating part→the first cultivating part) starts. If the circulation starts, light from the second light source 320 is emitted to illuminate the culture pipe 330 and the photosynthesis of photosynthetic microalgae contained in the culture solution is carried out. Flow rate of the circulated culture solution may be controlled with a flow rate controller coupled electronically to the pump in order to prevent attachment of photosynthetic microalgae, especially *Spirulina*, and maximize photosynthesis of circulating micro algae. The flow rate may be controlled between 1 to 50 cm/sec. More preferably the flow rate is 10 to 40 cm/sec. In the most preferred embodiment the flow rate is 20 to 30 cm/sec, but is not limited thereto.

During the circulatory cultivation of the photosynthetic microalgae, contamination of various germs originated from environment is prevented by applying positive pressure of about 0.1 to 1.0 $kgf/cm^2$ to the culture tank 101 of the first cultivating part 100 via injecting mixed gases of carbon dioxide and nitrogen to the culture tank 101 through the gas inlet 111 and pH of the culture solution is controlled by adjustment of partial pressure of carbon dioxide included in the mixed gases.

In addition, oxygen generated by the photosynthesis during the cultivation of photosynthetic microalgae is transferred to the top of the culture tank 101 after being separated from the culture solution at the culture tank 101 of the first cultivating part 100 and then the oxygen is emitted externally through the pressure-controlling valve 112. In this case, if the culture pipe 330 of the second cultivating part 200 is composed as a parallel multiple folded form including straight parts and curved parts on one frame, oxygen may be accumulated at the curved parts of the culture pipe 330. Thus, it is preferred to remove oxygen accumulated in the culture pipe 330 by attaching one or more oxygen dischargers at the curved parts.

When the circulatory cultivation of photosynthetic microalgae is terminated, the final culture solution including the photosynthetic microalgae is harvested by opening the final outlet 133 of the first cultivating part 100. After the termination of the cultivation, the present inventors confirmed remarkable results that at most 5% of inner surface of the culture pipe 330 is covered by the photosynthetic microalgae. Thus, the present inventors solved problem that the efficiency of cultivation is lowered via attachment of photosynthetic microalgae to inner surface of culture vessel by lowering rate of proliferating of photosynthetic microalgae through applying only light condition using light sources equipped along with culture pipe and by maximizing fluidity of culture solution via circulating the culture solution from the first cultivating part to the pump, from the pump to the second cultivating part and from the second cultivating part to the first cultivating part.

The photosynthetic microalgae may be genus *Chlorella*, genus *Gunaliella*, genus *Spirulina*, but is not limited thereto. More preferentially the photosynthetic microalga is genus *Spirulina*.

While the present invention has been described in connection with certain exemplary embodiments, it is to be understood that the invention is not limited to the disclosed embodiments but, on the contrary, is intended to cover various modifications and equivalent arrangements included within the spirit and scope of the appended claims, and equivalents thereof.

What is claimed is:

1. A photobioreactor comprising:
   a first cultivating part comprising a culture tank in which culture media are supplied and a first light source coupled to the culture tank so as to illuminate the inside of the culture tank;
   a second cultivating part comprising a culture pipe placed outside the culture tank and supplied with culture solution from the culture tank and a second light source coupled to the culture pipe so as to illuminate the inside of the culture pipe, wherein the culture pipe has a parallel multiple folded form including straight parts and curved parts and comprises a plurality of second light sources coupled to the outside of the culture pipe in the longitudinal direction of the culture pipe and the culture pipe is equipped with an oxygen discharger at the curved parts; and
   a pump part connected to both the first cultivating part and the second cultivating part so as to circulate the culture solution between the first cultivating part and the second cultivating part.

2. The photobioreactor according to claim 1, wherein the first light source is placed inside the culture tank.

3. The photobioreactor according to claim 1, wherein the first cultivating part further comprises at least one first culture solution inlet and at least one first culture solution outlet connected to both the culture tank and the pump part, and the second cultivating part further comprises at least one second culture solution inlet and at least one second culture solution outlet connected to the first culture solution outlet and to the second culture solution inlet, respectively through the pump part.

4. The photobioreactor according to claim 1, wherein the first cultivating part further comprises a fresh media inlet for supplying fresh media into the culture tank and a final outlet for releasing culture solution from the culture tank.

5. The photobioreactor according to claim 1, wherein the first cultivating part further comprises an agitator for mixing culture solution, which is coupled to the inside of the culture tank.

6. The photobioreactor according to claim 1, wherein the first cultivating part further comprises a pressure-controlling valve for controlling pressure in the culture tank.

7. The photobioreactor according to claim 1, wherein the first cultivating part further comprises a temperature controller for controlling temperature in the culture tank.

8. The photobioreactor according to claim 1, wherein the first cultivating part further comprises one or more ports for sensors coupled to the culture tank.

9. The photobioreactor according to claim 1, wherein the first cultivating part further comprises a gas inlet coupled to the culture tank so as to inject gases into the culture tank.

10. The photobioreactor according to claim 1, wherein the pump part further comprises a flow rate controller.

11. The photobioreactor according to claim 1, wherein the oxygen discharger comprises an earth sensor, a mass flow controller electrically connected to the earth sensor and a valve connected to the mass flow controller.

12. The photobioreactor according to claim 1, wherein the culture pipe has an inside diameter of 3 to 30 cm.

13. A photobioreactor comprising the followings:
    a first cultivating part comprising a culture tank in which culture media are supplied, a first media inlet, a first media outlet and a first light source coupled each to the culture tank; and
    a second cultivating part comprising a culture pipe arranged outside the culture tank in tubular shape and supplied with culture media from the culture tank, a second media inlet, a second media outlet and a plurality of second light sources coupled each to the culture pipe in the longitudinal direction of the culture pipe, wherein the culture pipe has a parallel multiple folded form including straight parts and curved parts and is equipped with an oxygen discharger at the curved parts,
    wherein the first media outlet is connected to the second media inlet and the first media inlet is connected to the second media outlet in order that the culture media can be circulated between the first cultivating part and the second cultivating part.

14. The photobioreactor according to claim 13, further comprising a pump part connected to both the first cultivating part and the second cultivating part in order to circulate culture solution between the first cultivating part and the second cultivating part.

15. The photobioreactor according to claim 14, wherein the pump part comprises
    a third culture solution inlet between the first culture solution outlet and the second culture solution inlet; and a third culture solution outlet between the first culture solution inlet and the second culture solution outlet.

16. The photobioreactor according to claim 13, wherein the pump part further comprises a flow rate controller.

17. The photobioreactor according to claim 13, wherein the culture pipe has an inside diameter of 3 to 30 cm.

* * * * *